(12) United States Patent
Chrapkova et al.

(10) Patent No.: US 12,252,685 B2
(45) Date of Patent: Mar. 18, 2025

(54) FERMENTATION SYSTEM, FEED CONTROLLER, AND RELATED METHODS

(71) Applicant: DSM IP ASSETS B.V., Heerlen (NL)

(72) Inventors: Natalia Chrapkova, Esbjerg N (DK); Peter Becker, Hørsholm (DK); Ted Johanson, Hørsholm (DK); Mikael Jansen, Esbjerg N (DK)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 18/709,000

(22) PCT Filed: Nov. 10, 2022

(86) PCT No.: PCT/EP2022/081507
§ 371 (c)(1),
(2) Date: May 9, 2024

(87) PCT Pub. No.: WO2023/083974
PCT Pub. Date: May 19, 2023

(65) Prior Publication Data
US 2024/0327777 A1    Oct. 3, 2024

(30) Foreign Application Priority Data

Nov. 11, 2021 (DK) .......................... PA 2021 70551

(51) Int. Cl.
*C12M 1/36* (2006.01)
*C12M 1/34* (2006.01)

(52) U.S. Cl.
CPC ............ *C12M 41/48* (2013.01); *C12M 41/32* (2013.01); *C12M 41/36* (2013.01)

(58) Field of Classification Search
CPC ....... C12M 41/48; C12M 41/32; C12M 41/36
(Continued)

(56) References Cited

U.S. PATENT DOCUMENTS 10,988,727 B2    4/2021   Blessing et al.
11,427,845 B2    8/2022   Jennewein
(Continued)

FOREIGN PATENT DOCUMENTS

| CA | 2651338 | 11/2007 |
|---|---|---|
| CN | 104093846 | 10/2014 |

(Continued)

OTHER PUBLICATIONS

International Search Report and Written Opinion issued for International Patent Application No. PCT/EP2022/081507, mailed Feb. 22, 2023, 14 pages.

(Continued)

*Primary Examiner* — Michael L Hobbs
(74) *Attorney, Agent, or Firm* — Neal, Gerber & Eisenberg LLP

(57) ABSTRACT

A feed control system and related methods for a heterologous product, such as a human milk oligosaccharide, fermentation system are disclosed. The feed control system comprises a feed controller. The feed controller comprises a processor and an interface. The processor is configured to obtain a biomass content in a fermentation broth. The processor is configured to determine a carbon input parameter based on the biomass content. The processor is configured to control a carbon input to the fermentation broth according to the carbon input parameter.

21 Claims, 7 Drawing Sheets

(58) Field of Classification Search
USPC .................................. 47/1.4; 435/290.1–290.4
See application file for complete search history.

(56) References Cited

U.S. PATENT DOCUMENTS

| | | | |
|---|---|---|---|
| 11,609,120 | B2 | 3/2023 | Webster et al. |
| 2009/0117647 | A1 | 5/2009 | Srinivasa et al. |
| 2010/0112242 | A1 | 5/2010 | Medoff |
| 2015/0010899 | A1 | 1/2015 | Riisgaard et al. |
| 2017/0253848 | A1* | 9/2017 | Emmerson ............... C12Q 3/00 |

FOREIGN PATENT DOCUMENTS

| | | | |
|---|---|---|---|
| CN | 108085248 | * 11/2016 | ............ C12M 21/04 |
| CN | 106459901 | 2/2017 | |
| CN | 107964506 | 4/2018 | |
| CN | 110643658 | 1/2020 | |
| CN | 111172329 | 5/2020 | |
| CN | 113403193 | 9/2021 | |
| EP | 0078500 | 5/1983 | |
| JP | 2012011382 | 1/2012 | |
| WO | WO 2009129655 | 10/2009 | |
| WO | WO 2019071076 | 4/2019 | |
| WO | WO 2019123324 | 6/2019 | |
| WO | WO 2021097281 | 5/2021 | |
| WO | WO 2023083974 | 5/2023 | |

OTHER PUBLICATIONS

Herring and Blattner 2004 J. Bacteriol. 186: 2673-81.
Warming et al 2005 Nucleic Acids Res. 33(4): e36.
Dumont et al 2016 Crit Rev Biotechnol 36(6): 1110-1122.
Genbank, "alpha-1,2-fucosyltransferase [Helicobacter pylori]", Accession No. WP_080473865.1, Mar. 28, 2017.
First Technical Report issued for DK Patent Application No. PA 2021 70551, dated May 12, 2022, 9 pages.
Dowd, J.E. et al.: "Optimization and control of perfusion cultures using a viable cell probe and cell specific perfusion rates", Cytotechnology, 2003, vol. 42, pp. 35-45.
Fourth Technical Report issued for DK Patent Application No. PA 2021 70551, dated Apr. 3, 2024, 2 pages.
Granted claims for DK Patent Application No. PA 2021 70551.

* cited by examiner

FERMENTATION SYSTEM, FEED CONTROLLER, AND RELATED METHODS

CROSS-REFERENCE TO RELATED APPLICATIONS

This application is a national stage entry pursuant to 35 U.S.C. § 371 of International Application No. PCT/EP2022/081507, filed on Nov. 10, 2022, which claims priority to Denmark Application No. PA 202170551, filed on Nov. 11, 2021, the entire contents of all of which are hereby incorporated by reference in their entirety.

The present disclosure relates to a fermentation system with a feed control system, feed controller and related methods. In particular, a method of producing oligosaccharides, such as human milk oligosaccharides (HMO), in a fermentation system is disclosed.

BACKGROUND

During a fermentation process of biomass in a fermenter or fermentation system, a change in the balance between the carbon input and the cell culture's respiratory capacity severely inhibits the cell culture which may ultimately lead to the loss of the batch. The change in balance can be caused by overfeeding or underfeeding of the cells with carbon input which in turn leads to a sub-optimal fermentation and outcome thereof. Challenges remain in reducing the risk of batch loss and in general improving the yield from a fermentation system, and in particular in the production of human milk oligosaccharides (HMO).

SUMMARY

Accordingly, there is a need for a feed control system, a feed controller, and methods for improving yield from fermentation systems producing heterologous compounds.

A feed control system for a fermentation system, such as heterologous compound fermentation system or a human milk oligosaccharide fermentation system, is provided. The feed control system comprises a feed controller. The feed controller comprises a processor and an interface. The processor is configured to obtain a biomass content in a fermentation broth. The processor is configured to determine a carbon input parameter based on the biomass content. The processor is configured to control a carbon input to the fermentation broth according to the carbon input parameter.

Further, a method for producing a heterologous product, such as human milk oligosaccharides (HMO), in a fermentation system is provided. The method comprises obtaining a biomass content in a fermentation broth comprising a host cell capable of producing the heterologous product. The method comprises determining a carbon input parameter based on the biomass content. The method comprises controlling a carbon input to the fermentation broth according to the carbon input parameter.

The present disclosure allows optimization of carbon input to a fermentation system which in turn may lead to optimized yield of the heterologous product, such as HMO.

It is an important advantage of the present disclosure that the risk of batch loss is reduced and/or yield of HMO production is improved. This is in particular important in large scale fermentation systems, where loss of batch and/or even a small increase in HMO yield has significant economic impact.

The use of in situ real-time online monitoring of biomass, e.g. using FTIR spectroscopy, allows a very precise determination of the biomass concentration or content in the fermentation broth of a large scale fermentation system.

Further, the combination of the biomass content monitoring with flow measurements of carbon and ammonia input allows safeguarding the E. coli fermentations against overfeeding and at the same time enables optimization of the HMO/carbon yield based on optimization of the carbon flow.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1:
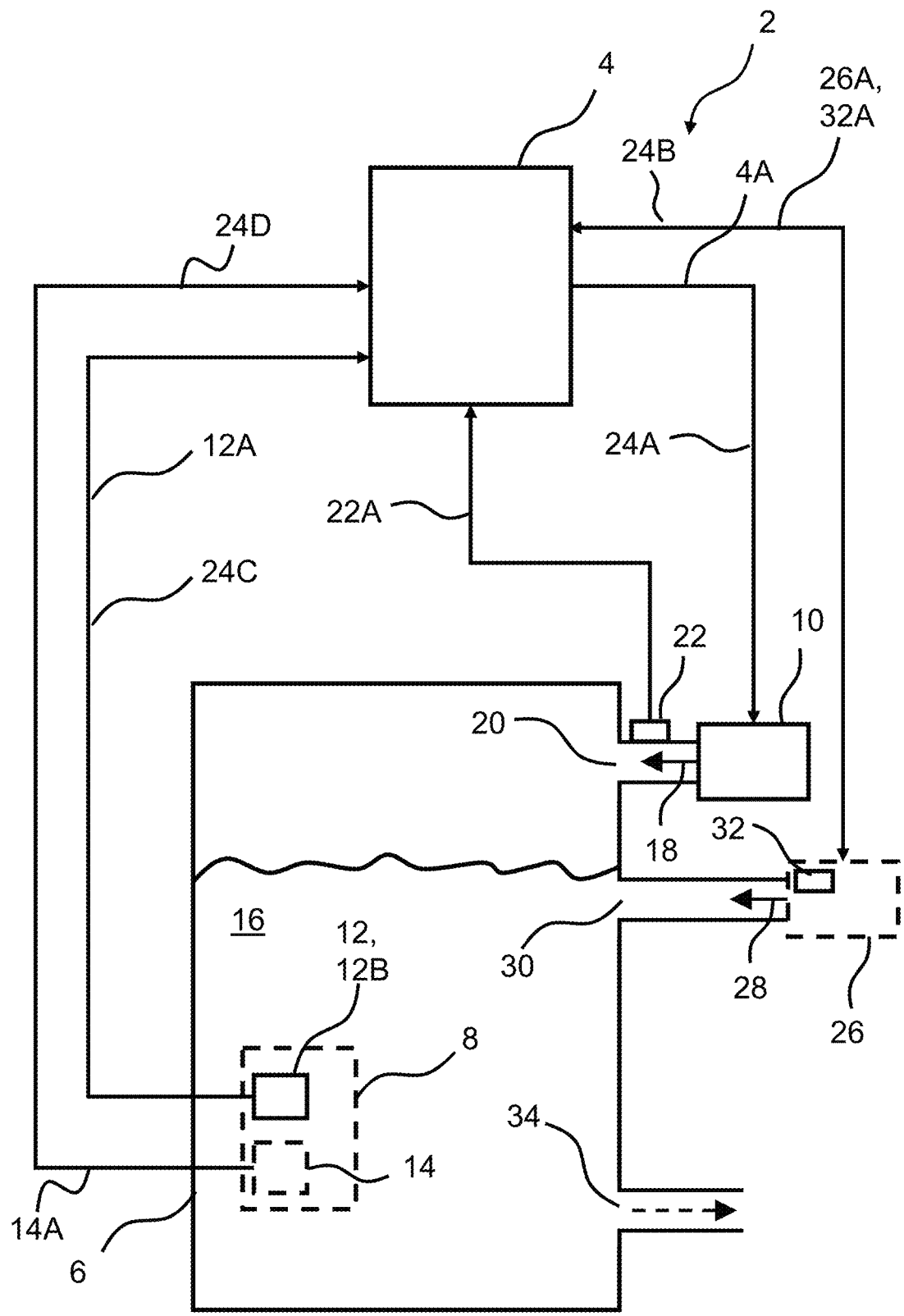
FIG. 1 schematically illustrates an exemplary fermentation system according to the present disclosure, FIG. 2 schematically illustrates exemplary feed controller/feed control system according to the present disclosure.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A feed control system for a fermentation system producing a heterologous compound is disclosed.

The fermentation system comprises a feed control system, a fermentation tank, a sensor system, and a carbon source. When the fermentation system is in operation, the fermentation tank will contain a fermentation broth comprising a growth media and one or more organism(s), such as host cells, capable of producing a heterologous product of interest. The organism constitutes the biomass content of the broth.

The fermentation system may be for the production of a heterologous product, such as one or more human milk oligosaccharides In the fermentation system, carbon, e.g. in the form of a sugar solution, glycerol, glucose, fructose, sucrose, or a combination thereof, is fed into the fermentation tank via a carbon input from the carbon source at a flow rate, either continuously or in discrete portions. The added carbon may be mixed with the fermentation broth, optionally by forced mixing. The flow rate of carbon into the fermentation tank may be based on and/or indicated/given by the carbon input parameter, also denoted CIP. In other words, the carbon input parameter may be a flow rate or indicative of a flow rate, such as a flow rate in the range from 1 kg/hour to 5,000 kg/hour. Thus, the carbon input parameter is optionally used as a control parameter from the feed control system to the carbon source supply system.

The fermentation tank accommodates a fermentation broth and comprises one or more inputs including a carbon input connected to the carbon source via appropriate pipe assembly. The fermentation tank may have a volume larger than 0.05 $m^3$, such as larger than 0.1 $m^3$, e.g., larger than 10 $m^3$. In one or more example systems/methods, the fermentation tank may have a volume in the range from 20 $m^3$ to 500 $m^3$. The fermentation broth may have an initial weight that is increased during fermentation to an end weight of the fermentation broth. In one or more exemplary fermentation systems, the fermentation broth has an initial weight larger than 10 tons, such as in the range from 20 tons to 70 tons. In one or more exemplary fermentation systems, the fermentation broth has an end weight larger than 100 tons, such as larger than 200 tons and optionally even larger than 300 tons.

The fermentation system comprises a sensor system. The sensor system is connected wirelessly and/or by wire to the feed control system for provision of sensor data to the feed control system/feed controller. The sensor system comprises one or more sensors including a first sensor or first sensor device connected wirelessly and/or by wire to the feed control system for provision of first sensor data to the feed control system/feed controller. The sensor system optionally includes a second sensor or second sensor device connected wirelessly and/or by wire to the feed control system for provision of second sensor data to the feed control system/feed controller.

The first sensor device and/the second sensor device may comprise or be an optical density meter, such as an optical density probe.

The first sensor device may be or comprise a spectrometer, such as a Fourier Transform Infrared (FTIR) spectrometer and/or a Raman spectrometer. In other words, the feed control system optionally comprises a Fourier Transform Infrared (FTIR) spectrometer and/or a Raman spectrometer connected to the feed controller for provision of spectrometer data (first sensor data) to the feed controller. The spectrometer data (first sensor data) may be indicative of the biomass content in the fermentation broth. An FTIR spectrometer and/or a Raman spectrometer advantageously provides accurate and substantially continuous (e.g. at least every 5 minutes) measurements of the biomass content in the fermentation tank allowing improved and more precise monitoring of the fermentation broth which in turn allows improved control of the fermentation and thus the HMO yield.

The first sensor device may be or comprise a turbidity probe and/or an IR sensor, such as a near-IR and/or a mid-IR sensor, for provision of first sensor data indicative of the biomass content in the fermentation broth to the feed controller.

The first sensor device may be or comprise an NMR sensor device for provision of first sensor data indicative of the biomass content in the fermentation broth to the feed controller.

The first sensor device may be or comprise a flow cytometry sensor device for provision of first sensor data indicative of the biomass content in the fermentation broth to the feed controller.

The first sensor device may be or comprise a microscopy sensor device for provision of first sensor data indicative of the biomass content in the fermentation broth to the feed controller.

In one or more exemplary fermentation systems, the first sensor device and/or the second sensor device comprises one or more sensors configured to measure/determine one or more electrical properties, e.g. impedance, such as resistance and/or capacitance, of the fermentation broth. In other words, the first sensor data and/or second sensor data may be indicative of one or more electrical properties of the fermentation broth.

In one or more exemplary fermentation systems, the first sensor device and/or the second sensor device comprises one or more sensors configured to measure/determine volume and/or weight of the fermentation broth. In other words, the first sensor data and/or second sensor data may be indicative of volume and/or weight of the fermentation broth.

The fermentation system comprises a carbon source supply system or device configured to input carbon/carbon source into the fermentation tank. The carbon source supply system is connected to the feed control system/processor for allowing control of the carbon input to the fermentation broth/fermentation tank according to the carbon input parameter. The carbon source supply system comprises one or more of vessel, tubing, valves, and pumps.

The feed control system comprises a feed controller comprising a processor and an interface. The interface may be a wired and/or wireless interface configured for connection with a sensor system, carbon source supply system, and optionally other entities of the fermentation system. The feed control system may comprise a display and/or an input device respectively connected to the interface. The feed control system may be a remote control system.

The processor is configured to obtain a biomass content of biomass in a fermentation broth. The biomass content is measured in terms of weight or concentration. In some examples, the biomass content is measured in kg/vol or kg. The biomass content may be based on first sensor data from first sensor/first sensor device and/or second sensor data from second sensor/second sensor device. The biomass content may be a normalized biomass content, e.g. as shown in equation (1) below.

In one or more examples, the biomass content may be based on an optical density (OD) provided as spectrometer data (first sensor data) multiplied with weight of fermentation broth FB_W, and optionally normalized for provision of the biomass content also denoted BC. The biomass content BC may be given as:

$$BC = \alpha \cdot OD \cdot FB\_W, \quad (1)$$

where $\alpha$ is a normalization factor and FB_W is optionally measured with sensor, such as second sensor/second sensor device, and/or determined based on feed rates applied during the fermentation process.

The processor is configured to control a carbon input (such as sugar solution, glycerol, glucose, fructose, sucrose, or a combination thereof) to the fermentation broth according to the carbon input parameter. To control a carbon input optionally comprises outputting the carbon input parameter via the interface to the carbon source supply system. The carbon source supply system feeds carbon to the fermentation tank via a carbon input, e.g. by controlling a valve and/or a pump of the carbon source supply system according to the carbon input parameter.

In one or more exemplary feed control systems, to determine a carbon input parameter, such as the configuration or act to determine a carbon input parameter, comprises to determine a feed rate also denoted FR. The feed rate may be indicative of a carbon feed rate per biomass, such as a carbon source feed rate per biomass. The carbon input parameter may be based on the feed rate. The feed rate may be based on the biomass content. In other words, the processor may be configured to determine a feed rate indicative of a carbon feed rate per biomass; and to determine a carbon input parameter based on the feed rate and the biomass content.

The processor is optionally configured to determine a carbon input parameter based on the feed rate and/or the biomass content. In one or more exemplary feed control systems, the carbon input parameter CIP is given as $$CIP = BC \cdot FR, \quad (2)$$

where BC is the biomass content and FR is feed rate indicative of a carbon feed rate per biomass.

It may be desirable to implement minimum and/or maximum values for the carbon input parameter, e.g. in order to secure a minimum growth and/or implement system capacity limits. Thus, in one or more exemplary feed control systems, to determine a carbon input parameter based on the feed rate and the biomass content, such as the configuration or act to determine a carbon input parameter based on the feed rate and the biomass content, may comprise to determine a preliminary carbon input parameter also denoted PCIP and optionally given as $$PCIP = BC \cdot FR. \quad (3)$$

In other words, the processor may be configured to determine a preliminary carbon input parameter based on the feed rate and the biomass content. The carbon input parameter may be based on the preliminary carbon input parameter. The preliminary carbon input parameter may be used as the carbon input parameter if within minimum and maximum values. A lower value or an upper value of an acceptable range for the carbon input parameter may be applied if the preliminary carbon input parameter is not within a suitable/desired range.

In one or more exemplary feed control systems, to determine a carbon input parameter, such as the configuration or act to determine a carbon input parameter, comprises to set the preliminary carbon input parameter as the carbon input parameter in accordance with the preliminary carbon input parameter satisfying a carbon input criterion. The carbon input criterion may be based on a minimum flow rate of carbon and/or a maximum flow rate of carbon. In other words, the processor may be configured to set the preliminary carbon input parameter as the carbon input parameter in accordance with the preliminary carbon input parameter satisfying a carbon input criterion.

In one or more exemplary feed control systems, to determine a carbon input parameter comprises to set a default carbon input parameter, such as a maximum flow rate of carbon, as the carbon input parameter in accordance with the preliminary carbon input parameter not satisfying the carbon input criterion.

In other words, the carbon input parameter CIP may be given as:

$$CIP = \begin{cases} PCIP = BC \cdot FR & \text{if } PCIP < CIP\_MAX \\ CIP\_MAX & \text{if } PCIP \geq CIP\_MAX \end{cases}, \quad (4)$$

where CIP_MAX is a maximum flow rate of carbon into the fermentation tank and PCIP<CIP_MAX is the carbon input criterion.

In some examples, when the preliminary carbon input parameter, is below a minimum flow rate of carbon, the minimum flow rate of carbon may be set as the carbon input parameter. In other words, the carbon input parameter CIP may be given as:

$$CIP = \begin{cases} CIP\_MIN & \text{if } PCIP \leq CIP\_MIN \\ PCIP = BC \cdot FR & \text{if } CIP\_MIN < PCIP < CIP\_MAX, \\ CIP\_MAX & \text{if } PCIP \geq CIP\_MAX \end{cases} \quad (5)$$

where CIP_MIN is a minimum flow rate of carbon, CIP_MAX is a maximum flow rate of carbon into the fermentation tank, and CIP_MIN<PCIP<CIP_MAX is the carbon input criterion.

The maximum flow rate of carbon CIP_MAX and the minimum flow rate of carbon CIP_MIN may be indicative of a flow rate range of carbon during the fermentation. In one or more exemplary feed control systems, the maximum flow rate of carbon and/or the minimum flow rate of carbon are adaptive, i.e. may change over time, e.g. as a function of time.

In one or more exemplary feed control systems, the maximum flow rate of carbon is a function of time and is optionally given by $$CIP\_MAX = f\_max(t) = K\_CIP\_2 \cdot t^2 + K\_CIP\_1 \cdot t + K\_CIP\_0, \quad (6)$$

where K_CIP_0, K_CIP_1, and K_CIP_2 are polynomial coefficients, and the time t may be time since start of fermentation or start of feeding.

In one or more exemplary feed control systems, the maximum flow rate of carbon is a polynomial function of time, such as a first order or second order polynomial function.

In one or more exemplary feed control systems, where the maximum flow rate of carbon is a first order polynomial function of time, the coefficient K_CIP_1<0.

In one or more exemplary feed control systems, where the maximum flow rate of carbon is a second order polynomial function of time, the coefficient K_CIP_2<0.

In one or more exemplary feed control systems, where the maximum flow rate of carbon (kg/hour) is a second order polynomial function of time (given in minutes/60), the coefficient K_CIP_2<0, such as in the range from −2 to −0.001.

In one or more exemplary feed control systems, where the maximum flow rate of carbon (kg/hour) is a second order polynomial function of time (given in minutes/60), the coefficient K_CIP_1>0, such as in the range from 10 to 1,000, e. in the range from 20 to 100.

In one or more exemplary feed control systems, where the maximum flow rate of carbon or carbon source (kg/hour) is a second order polynomial function of time (given in minutes/60), the coefficient K_CIP_0>0, such as in the range from 10 to 1,000, e. in the range from 50 to 500.

In one or more exemplary feed control systems, to determine a feed rate FR indicative of a carbon feed rate per biomass, such as the configuration or act to determine a feed rate FR indicative of a carbon feed rate per biomass, comprises to apply a yield model, e.g. a HMO yield model, for provision of the feed rate FR or a preliminary feed rate PFR. The yield model may take one or more of biomass content and one or more operating parameters of the fermentation system as input. The feed rate may be based on the preliminary feed rate. The yield model may be a look-up table, e.g. mapping a given biomass content to a feed rate FR or a preliminary feed rate PFR. The yield model may be a function of one or more variables, such as biomass content and/or time. In other words, the processor may be configured to apply a yield model, e.g. a HMO yield model, for provision of the feed rate FR or a preliminary feed rate PFR.

In one or more exemplary feed control systems, to determine a feed rate indicative of a carbon feed rate per biomass, such as the configuration or act to determine a feed rate indicative of a carbon feed rate per biomass, comprises to determine a preliminary feed rate PFR. The preliminary feed rate PFR may be based on or be a function of time and/or biomass content and is optionally given by $$PFR = g(BC) = K\_FR\_2 \cdot BC^{\wedge}2 + K\_FR\_1 \cdot BC + K\_FR\_0, \quad (7)$$

Where K_FR_0, K_FR_1, and K_FR_2 are polynomial coefficients and BC is the biomass content. Thus, the yield model may be a polynomial function of biomass content, such as a first order or second order polynomial function.

In one or more exemplary feed control systems, where the preliminary feed rate PFR is a first order polynomial function of time, the coefficient K_FR_1<0.

In one or more exemplary feed control systems, where the preliminary feed rate PFR is a second order polynomial function of time, the preliminary feed rate PFR may be a decreasing function, at least in the time frame of fermentation or from a certain point in time in the time frame of fermentation.

In one or more exemplary feed control systems, where the preliminary feed rate PFR is a second order polynomial function, the coefficient K_FR_2 may be larger than 0, such as in the range from 0.01 to 5, and K_FR_1 may be less than 0, such as in the range from −5 to −0.01.

In one or more exemplary feed control systems, where the preliminary feed rate PFR is a second order polynomial function, the coefficient K_FR_2 may be less than 0 and K_FR_1 may be larger than 0.

In one or more exemplary feed control systems, where the preliminary feed rate PFR is a second order polynomial function, the coefficient K_FR_0 may be larger than 0, such as in the range from 10 to 1,000, e. in the range from 50 to 500.

In some examples, the yield model may be a PD regulation, a look-up table, and/or a HMO yield model. The yield model may be a function. Other yield models may be applied.

In one or more exemplary feed control systems, to determine a feed rate indicative of a carbon feed rate per biomass, such as the configuration or act to determine a feed rate indicative of a carbon feed rate per biomass, comprises to determine a maximum feed rate. In other words, the processor may be configured to determine a maximum feed rate. The maximum feed rate FR_MAX may be based on or be a function of time and/or biomass content and is optionally given by $$FR\_MAX = g_{max(BC)} = K\_FRM\_2 \cdot BC^{\wedge}2 + K\_FRM\_1 \cdot BC + K\_FRM\_0 \quad (8)$$

In one or more exemplary feed control systems, where the maximum feed rate FR_MAX is a first order polynomial function of time, the coefficient K_FRM_1<0.

In one or more exemplary feed control systems, where the maximum feed rate FR_MAX is a second order polynomial function of time, the maximum feed rate FR_MAX may be a decreasing function, at least in the time frame of fermentation.

In one or more exemplary feed control systems, the maximum feed rate FR_MAX may be a decreasing function, at least after an initial fermentation period. The initial fermentation period may be in the range from 5 hours to 60 hours.

In one or more exemplary feed control systems, where the maximum feed rate FR_MAX is a second order polynomial function, the coefficient K_FRM_2 may be larger than 0, such as in the range from 0.01 to 5, and K_FRM_1 may be less than 0, such as in the range from −5 to −0.01.

In one or more exemplary feed control systems, where the maximum feed rate FR_MAX is a second order polynomial function, the coefficient K_FRM_2 may be less than 0 and K_FRM_1 may be larger than 0.

In one or more exemplary feed control systems, where the maximum feed rate FR_MAX is a second order polynomial function, the coefficient K_FRM_0 may be larger than 0, such as in the range from 10 to 1,000, e. in the range from 50 to 500.

In one or more exemplary feed control systems, the feed rate is based on the maximum feed rate.

In one or more exemplary feed control systems, to determine a feed rate, such as the configuration or act to determine a feed rate, comprises to set the preliminary feed rate as the feed rate in accordance with the preliminary feed rate satisfying a feed rate criterion and/or to set a default feed rate as the feed rate, e.g. in accordance with the preliminary feed rate not satisfying the feed rate criterion. In other words, the processor may be configured to set the preliminary feed rate as the feed rate in accordance with the preliminary feed rate satisfying a feed rate criterion and/or to set a default feed rate as the feed rate, e.g. in accordance with the preliminary feed rate not satisfying the feed rate criterion.

For example, the feed rate may be given as $$FR = \begin{cases} PFR & \text{if } PFR < FR\_MAX \\ FR\_MAX & \text{if } PFR \geq FR\_MAX \end{cases}, \quad (9)$$

where PFR is a preliminary feed rate obtained from the yield model, and FR_MAX is a maximum feed rate based on the biomass content. Thus, FR_MAX may be seen as a default feed rate and PFR<FR_MAX may be seen as the feed rate criterion.

In one or more exemplary feed control systems, the processor may be configured to obtain a first operating parameter of the fermentation system, such as an ammonia/carbon parameter also denoted ACP. The first operating parameter may be given in gram ammonia per kg sugar. The first operating parameter may be a carbon/ammonia parameter also denoted carbon/ammonia ratio. The feed rate may be based on first operating parameter (ammonia/carbon parameter). The ammonia/carbon parameter is indicative of ammonia/carbon ratio, such as a ratio between ammonia feed rate and sugar (carbon source) feed rate into the fermentation tank/fermentation broth or a ratio between amounts of ammonia and sugar (carbon source) added to the fermentation in a given time period. In some examples, the ammonia/sugar ratio may be measured as grams of ammonia per kilogram carbon source/sugar. In other words, the processor may be configured to obtain one or more operating parameters including a first operating parameter of the fermentation system, wherein the carbon input parameter is optionally based on the first operating parameter and/or further operating parameter(s). The ammonia/carbon parameter may be a ratio between the flow rate of ammonia and the flow rate of carbon into the fermentation tank. The sensor system may comprise a first flow sensor for provision of first flow data optionally indicative of the flow rate of carbon/carbon source into the fermentation tank. The sensor system may comprise a second flow sensor for provision of second flow data optionally indicative of the flow rate of ammonia into the fermentation tank. Thus, the ammonia/carbon parameter is indicative of a ratio between ammonia and carbon source added to the fermentation tank, e.g. the flow rate of ammonia and the flow rate of carbon source into the fermentation tank. The ammonia/carbon parameter can be given or determined as a ratio between the flow rate of ammonia and the flow rate of carbon source into the fermentation tank or given or determined as a ratio between an amount of ammonia and an amount carbon source added into the fermentation tank in a given time period.

In one or more exemplary feed control systems, the processor may be configured to determine a maximum first operating parameter, such as a maximum ammonia/carbon parameter. The maximum ammonia/carbon parameter may be indicative of a maximum acceptable ammonia/carbon ratio in the fermentation broth. The processor may be configured to determine a minimum first operating parameter, such as a minimum ammonia/carbon parameter. The minimum first operating parameter and/or the maximum first operating parameter are optionally based on a time parameter indicative of a start of fermentation.

In one or more exemplary feed control systems, the feed rate is based on the first operating parameter and one or both of the maximum first operating parameter and the minimum first operating parameter.

In one or more exemplary feed control systems, the feed rate is based on the ammonia/carbon parameter and the maximum ammonia/carbon parameter. In some examples, the maximum ammonia/carbon ratio may be less than 90 grams of ammonia per 1 kg sugar. The maximum ammonia/carbon parameter is optionally based on a time parameter indicative of a start of fermentation. The maximum ammonia/carbon parameter is indicative of a maximum ratio between ammonia and carbon source added to the fermentation. Implementation of a maximum ammonia/carbon parameter allows the system to detect and reduce the risk of overfeeding the system. The maximum ammonia/carbon parameter ACP_MAX may be based on or be a function of time and/or biomass content and is optionally given by:

$$ACP\_MAX = h_{max(t)} = K\_ACM\_2\, t^2 + K\_ACM\_1 t + K\_ACM\_0 \quad (10)$$

where t is a time parameter indicative of a start of fermentation and K_ACM_2, K_ACM_1, and K_ACM_0 are function parameters/coefficients.

In one or more exemplary feed control systems, the maximum ammonia/carbon parameter ACP_MAX is a polynomial function of time, such as a first order or second order polynomial function.

In one or more exemplary feed control systems, where the maximum ammonia/carbon parameter ACP_MAX is a first order polynomial function of time or a second order polynomial function of time, the coefficient K_ACM_1<0.

In one or more exemplary feed control systems, where the maximum ammonia/carbon parameter ACP_MAX is a second order polynomial function of time, the coefficient K_ACM_2>0, such as in the range from 0.001 to 2.

In one or more exemplary feed control systems, where the maximum ammonia/carbon parameter ACP_MAX is a second order polynomial function of time, the coefficient K_ACM_2<0, such as in the range from −2 to −0.001.

In one or more exemplary feed control systems, where the maximum ammonia/carbon parameter ACP_MAX is a second order polynomial function of time (e.g. given in minutes/60), the coefficient K_ACM_1<0, such as in the range from −10 to −0.001, e. in the range from −2 to −0.01.

In one or more exemplary feed control systems, where the maximum ammonia/carbon parameter ACP_MAX is a second order polynomial function of time (given in minutes/60), the coefficient K_ACM_0>0, such as in the range from 10 to 1,000, e. in the range from 50 to 200.

In one or more exemplary feed control systems, to determine a feed rate comprises to set the preliminary feed rate as the feed rate in accordance with the first operating parameter, such a ACP, satisfying an operating criterion and/or to set a default feed rate or reduced feed rate as the feed rate, e.g. in accordance with the first operating parameter, such a ACP, not satisfying an operating criterion.

For example, the feed rate FR may be given as:

$$FR = \begin{cases} PFR & \text{if } ACP < ACP\_MAX \\ PFR\_RED & \text{if } ACP \geq ACP\_MAX \end{cases}, \quad (11)$$

where PFR is a preliminary feed rate obtained from the yield model or adjusted based on maximum feed rate, ACP is a first operating parameter (ammonia/carbon ratio) and ACP_MAX is a maximum ammonia/carbon parameter, and PFR_RED is a reduced preliminary feed rate, e.g. based on the preliminary feed rate or a default feed rate. Thereby, overfeeding the system may be avoided in turn reducing the risk of batch failure and/or increasing the yield.

In case the first operating parameter is a carbon/ammonia parameter CAP (carbon/ammonia rate), the feed rate FR may be given as:

$$FR = \begin{cases} PFR & \text{if } CAP > CAP\_MIN \\ PFR\_RED & \text{if } CAP \leq CAP\_MIN \end{cases} \quad (11A)$$

where PFR is a preliminary feed rate obtained from the yield model or adjusted based on maximum feed rate, CAP is a first operating parameter (carbon/ammonia ratio) and CAP_MIN is a minimum carbon/ammonia parameter, and PFR_RED is a reduced preliminary feed rate, e.g. based on the preliminary feed rate or a default feed rate. Thereby, overfeeding the system may be avoided in turn reducing the risk of batch failure and/or increasing the yield.

In one or more exemplary feed control systems, the processor may be configured to obtain the biomass content of biomass in the fermentation broth (with first sensor) at least once every 4 hours, e.g. at least two times per hour. For example, the processor may be configured to obtain the biomass content of biomass in the fermentation broth at least once every 15 minutes, such as once every 10 minutes, once every 5 minutes, once every 4 minutes, once every 3 minutes, once every 2 minutes or once every 1 minute.

A method of producing a heterologous product, such as human milk oligosaccharides, in a fermentation system is disclosed, the method comprises obtaining, optionally at least every 15 minutes, a biomass content in a fermentation broth comprising an organism capable of producing the heterologous, e.g. with a first sensor device comprising or being an FTIR sensor. The method comprises determining a carbon input parameter based on the biomass content. The carbon input parameter may be indicative of flow rate of carbon input to a fermentation tank of the fermentation system, e.g. indicated in kg/hour. The method comprises controlling a carbon input to the fermentation broth according to the carbon input parameter. It is to be noted that descriptions of the feed controller/processor also applies to corresponding operations, steps or act of the method of producing a heterologous product as disclosed herein.

The biomass being monitored in the fermentation system in the present invention is derived from the growth of a desired organism. For the production of a heterologous product such an organism is also termed a host cell. Suitable host cells for production of a heterologous product are known in the art. These may be bacterial or fungal host cells or mammalian cell lines which can be genetically engineered to produce the desired heterologous product.

Regarding the bacterial host cells, there are, in principle, no limitations; they may be eubacteria (gram-positive or gram-negative) or archaebacteria, as long as they allow genetic manipulation for insertion of a gene or regulatory element of interest and can be cultivated on a manufacturing scale. Preferably, the host cell has the property to allow cultivation to high cell densities.

Non-limiting examples of bacterial host cells that are suitable for recombinant industrial production of a heterologous product could be *Erwinia herbicola* (*Pantoea agglomerans*), *Citrobacter freundii, Pantoea citrea, Pectobacterium carotovorum,* or *Xanthomonas campestris*. Bacteria of the genus *Bacillus* may also be used, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus,* and *Bacillus circulans*. Similarly, bacteria of the genera *Lactobacillus* and *Lactococcus* may be engineered using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii,* and *Lactococcus lactis*. *Streptococcus thermophiles* and *Proprionibacterium freudenreichii* are also suitable bacterial species for the invention described herein. Also included as part of this invention are strains, engineered as described here, from the genera *Enterococcus* (e.g., *Enterococcus faecium* and *Enterococcus thermophiles*), *Bifidobacterium* (e.g., *Bifidobacterium longum, Bifidobacterium infantis,* and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*).

Non-limiting examples of fungal host cells that are suitable for recombinant industrial production of a heterologous product could be yeast cells, such as *Komagataella phaffii, Kluyveromyces lactis, Yarrowia lipolytica, Pichia pastoris,* and *Saccaromyces cerevisiae* or filamentous fungi such as *Aspargillus* sp, *Fusarium* sp or *Thricoderma* sp, exemplary species are *A. niger, A. nidulans, A. oryzae, F. solani, F. graminearum* and *T. reesei*.

Non-limiting examples of mammalian cell lines are chinese hamster ovary cells (CHO) and murine myeloma cells (NS0, Sp2/0), baby hamster kidney cells (BHK), Murine C127, human cell lines such as PER.C6, HKB-11, CAP and HuH-7, HEK293, HT-1080 and HeLa cells (see for example Dumont et al 2016 Crit Rev Biotechnol 36(6): 1110-1122).

In one or more exemplary embodiments, the host cell is selected from the group consisting of *E. coli, C. glutamicum, L. lactis, B. subtilis, S. lividans, P. pastoris,* and *S. cerevisiae*.

In one or more exemplary embodiments, the host cell is selected from the group consisting of *B. subtilis, S. cerevisiae* and *Escherichia coli*.

In one or more exemplary embodiments, the host cell is *B. subtilis*.

In one or more exemplary embodiments, the host cell is *S. cerevisiae*.

In one or more exemplary embodiments, the host cell is *Escherichia coli*.

A heterologous product in the context of the present invention is a compound which is either directly expressed from one or more heterologous gene inserted into a host cell or where one or more metabolic pathways of the cell and/or enzymatic activities in the cell have been engineered to produce a compound of interest. Heterologous products can for example be proteins, peptides, lipids, fatty acids, oligosaccharides, polysaccharides, polyesters or vitamins.

Heterologous produced proteins or polypeptides are for example biopharmaceutical compounds such as antibodies, vaccines, cytokines, blood factors, enzymes, hormones and growth factors, or industrial compounds such as enzymes.

These are generally produced by inserting a recombinant gene(s) that that encode the desired protein or polypeptide into the host cell.

Heterologous oligosaccharides and polysaccharides are for example human milk oligosaccharides (HMOs) or biopolymers. These are generally produced by inserting genes encoding enzymes that can produce the desired compounds based on precursor molecules provided to the cell or produced by synthetic pathways in the host cell (which also may be genetically engineered).

In a preferred embodiment of the present invention, the heterologous product is one or more human milk oligosaccharides (HMOs). HMOs are complex carbohydrates found in human breast milk. The HMOs have a core structure comprising a lactose unit at the reducing end that can be elongated by one or more beta-N-acetyl-lactosaminyl and/or one or more beta-lacto-N-biosyl units, and this core structure can be substituted by an alpha-L-fucopyranosyl and/or an alpha-N-acetyl-neuraminyl (sialyl) moiety.

In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-triose 2 (LNT-2) lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3'-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), 3'-O-sialyllacto-N-tetraose a (LST a), fucosyl-LST a (FLST a), 6'-O-sialyllacto-N-tetraose b (LST b), fucosyl-LST b (FLST b), 6'-O-sialyllacto-N-neotetraose (LST c), fucosyl-LST c (FLST c), 3'-O-sialyllacto-N-neotetraose (LST d), fucosyl-LST d (FLST d), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT). See for example Bych et al 2019 Current Opinion in Biotechnology 56:130-137 for a review on HMO production.

Lipids, fatty acids, polyesters and vitamins are like with the saccharides produced by manipulating the enzymatic expression and methanolic pathways of the host cell.

In one or more example methods, the parameters biomass content in a fermentation broth and carbon input parameter based on the biomass content are demined using the feed control system as disclosed herein.

In one or more example methods, the carbon input to the fermentation broth according to the carbon input parameter is controlled using the feed control system as disclosed herein.

In one or more example methods, the heterologous product is one or more human milk oligosaccharides. In one or more example methods, the host cell is *E. coli*.

The present disclosure further relates to a fermentation system which is a continuous and/or a semi-continuous fermentation system, e.g., a feed and bleed system. I.e., the heterologous product(s) producing microorganisms are cultivated in a continuous mode. The present disclosure in particular relates to a continuous and/or a semi-continuous fermentation system for producing HMOs.

In one or more example methods, the present disclosure relates to a fermentation system with a feed control system as described herein which is a continuous and/or a semi-continuous fermentation system. I.e., the heterologous product(s) producing microorganisms, e.g., producing HMOs, are cultivated in a continuous and/or semi-continuous mode.

As is shown in Example 2, the efficiency of a large-scale fermentation process can be increased even further by extending the fermentation time by shifting from fed-batch fermentation to a continuous and/or a semi-continuous fermentation system, such as to a feed and bleed fermentation, when the main fermentation vessel is reaching its maximum capacity.

In the current context, the phrase "continuous fermentation method/system/process" or "semi-continuous fermentation method/system/process" is used to describe a fermentation method/system/process wherein the contents of the reactor continuously or semi-continuously flow through the bioreactor. A continuous fermentation process is characterized by a defined, constant and continuous rate of feeding of fresh culture medium into the bioreactor, whereby culture broth is at the same time removed from the bioreactor at the same defined, constant and continuous removal rate. In some example methods, the combination of the feed of the carbon source, with the removal of at least a portion of the oligosaccharide preparation are performed concurrently.

Typically, a continuous and/or a semi-continuous fermentation method according to the present invention comprises,
  a. providing a first primary bioreactor comprising a liquid nutrient media,
  b. inoculating the first primary bioreactor with one or more heterologous product producing microorganism(s),
  c. adding to said first primary bioreactor a carbon source,
  d. fermenting the added carbon source to produce a fermentation broth comprising at least one or more heterologous product producing microorganism(s) and one or more heterologous product(s),
  e. passing at least a portion of the fermentation broth from the first primary bioreactor, via a central bleed line into at least one other bioreactor and/or storage tank,
  f. further adding at least a portion of additional liquid nutrient media and/or carbon source to the first primary bioreactor,
  g. operating the first primary bioreactor at conditions to promote growth of microorganisms and to promote heterologous product production from said microorganism and optionally,
  h. harvesting and/or purifying the one or more heterologous product(s) from the fermentation broth.

In the above process the order of step b. and c. can be reversed. In addition to the carbon source, a substrate needed for the heterologous product formation may optionally be added along with the carbons source in step c and f above, either as a separate feed or together with the carbon source.

Typically, passing of fermentation broth from the first primary bioreactor into the at least one other bioreactor and/or storage tank, as well as the addition of additional liquid and/or carbon source, is continuous. The volume of liquid media and/or carbon source added is either lower, higher or equals the amount of fermentation broth passed from the first primary bioreactor into the at least one other bioreactor and/or storage tank.

In one or more example methods, the continuous fermentation method according to the present disclosure comprises,
a. providing a first primary bioreactor comprising a liquid nutrient media,
b. inoculating the first primary bioreactor with one or more heterologous product producing microorganism(s),
c. continuously adding to said first primary bioreactor a carbon source,
d. fermenting the added carbon source to produce a fermentation broth comprising at least one or more heterologous product producing microorganism(s) and one or more heterologous product(s),
e. when the volume in the first primary bioreactor reaches a pre-defined volume, a portion of the fermentation broth from the first primary bioreactor is continuously passed to at least one other bioreactor and/or storage tank via a central bleed line,
f. continuously adding additional liquid nutrient media and/or carbon source to the first primary bioreactor to maintain the pre-defined volume in step e.,
g. operating the first primary bioreactor at conditions to promote growth of microorganisms and to promote heterologous product production from said microorganism while maintaining the pre-defined volume and optionally,
h. harvesting and/or purifying the one or more heterologous product(s) from the fermentation broth in the first primary bioreactor and/or the other bioreactor and/or storage tank.

In addition to the carbon source, a substrate needed for the heterologous product formation may optionally be added along with the carbons source in step c and f above, either as a separate feed or together with the carbon source.

The pre-defined volume in the first primary bioreactor can be a volume range which is between the maximum capacity of the first primary bioreactor and 20%, such as 10% such as 5% below the maximum capacity of first primary bioreactor.

The addition of additional liquid and/or carbon source, and the passing of fermentation broth from the first primary bioreactor, can be performed via a central bleed line into at least one other bioreactor and/or storage tank, and can be controlled by a control unit according to the present invention, linking the flow rate of the addition of liquid and carbon source to the flow rate of and the passing of fermentation broth from the first primary bioreactor, via a central bleed line into at least one other bioreactor and/or storage tank.

Typically, the initial level of liquid media in the first primary bioreactor (step a.) is 10-25%, 26-50%, 51-75% or 76-100% of the total bioreactor volume, the adding of additional liquid and/or carbon source to the first primary is initiated (step c.) when the fermentation broth constitutes 10-25%, 26-50%, 51-75% or 76-95% of the total bioreactor volume, and passing of the fermentation broth from the first primary bioreactor (step e.), via a central bleed line into at least one other bioreactor and/or storage tank of liquid media in the first primary bioreactor is initiated when the fermentation broth constitutes 10-25%, 26-50%, 51-75% or 76-100% of the total bioreactor volume.

In one or more examples of the present invention, the initial level of liquid media is below 50% or 75% of the total bioreactor volume, and the addition of additional liquid and/or carbon source to the first primary is (step c.) continued until approximately 80 to 100% of the total bioreactor volume is reached and then the passing of the fermentation broth from the first primary bioreactor (step e.), via a central bleed line to at least one other bioreactor and/or storage tank is initiated.

In one or more examples of the present invention, the initial level of liquid media is below between 75% and 95% of the total bioreactor volume, and the addition of additional liquid and/or carbon source to the first primary is (step c.) is done simultaneously with the passing of the fermentation broth from the first primary bioreactor (step e.), via a central bleed line to at least one other bioreactor and/or storage tank.

FIG. 1 shows an exemplary fermentation system implementing the feed control system according to the present disclosure. The fermentation system 2 comprises a feed control system 4, a fermentation tank 6, a sensor system 8, and a carbon source supply system 10.

The sensor system 8 comprises a first sensor 12, e.g., an FTIR spectrometer, for provision of first sensor data 12A such as spectrometer data. An optical density probe 12B or other sensor, such as a capacitance sensor, may be used as the first sensor 12. The sensor system 8 optionally comprises a second sensor 14 for provision of second sensor data 14A. The second sensor 14, e.g., implemented as a pressure and/or level sensor, may be configured to measure, sense or detect the amount of fermentation broth 16 in the fermentation tank 6. The sensors 12, 14 are wired or wirelessly connected to the feed control system 4, e.g. via a network, for provision of sensor data 12A, 14A to the feed control system 4. Thus, the feed control system 4 is configured to obtain a biomass content, e.g. based on first sensor data 12A and optionally second sensor data 14A, of biomass in the fermentation broth 16 of the fermentation tank 6.

The fermentation system 2 comprises a carbon source supply system 10. The carbon source supply system 10 is wired or wirelessly connected to the feed control system 4, e.g. via a network, for communicating with the feed control system including receiving the carbon input parameter 4A for control of carbon flow 18, such as sugar solution, glycerol, fructose, glucose, sucrose, or a combination thereof into the fermentation tank 6 via carbon input 20 of the fermentation tank 6. The sensor system optionally comprises a first flow sensor 22 for measuring the carbon flow 18 and provision of first flow data 22A indicative of the flow rate of carbon into the fermentation tank 6. The first flow sensor 22 may be integrated into the carbon source 10 which then provides the first flow data 22A to the feed control system 4 via data connection 24A.

The fermentation system 2 optionally comprises an ammonia source 26 or other source configured for regulating pH in the fermentation broth 16. The ammonia source 26 may be wired or wirelessly connected to the feed control system 4, e.g. via a network, for communicating with the feed control system including receiving an ammonia input parameter 26A for control of ammonia flow 28 of ammonia into the fermentation tank 6 via ammonia input 30 of the fermentation tank 6. The sensor system optionally comprises a second flow sensor 32 for measuring the ammonia flow 28 and provision of second flow data 32A indicative of the flow rate of carbon into the fermentation tank 6. The second flow sensor 32 is optionally as illustrated integrated into the ammonia source 26 which then provides the second flow data 32A to the feed control system 4 via data connection 24B.

The fermentation tank 6 may be emptied via tank output 34 during and/or after the fermentation process.

Figure 2:
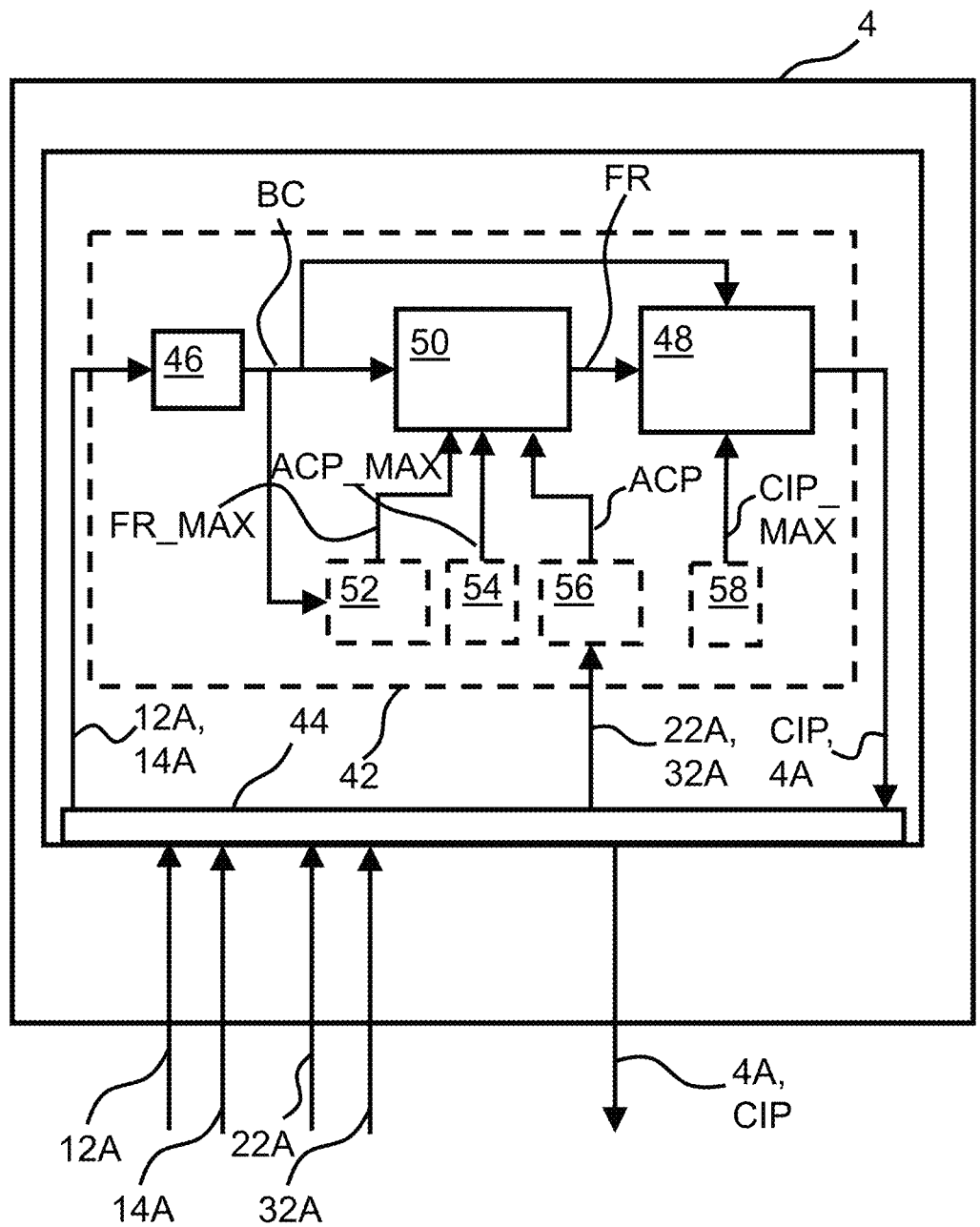

FIG. 2 shows an exemplary feed control system according to the present disclosure. The feed control system 4 comprises a feed controller 40 comprising a processor 42 and an interface 44.

The feed control system 4 communicates with entities, such as sensor system, carbon source, and optionally ammonia source and receives sensor data 12A, 14A, 22A, 32A from sensors of the sensor system/fermentation system via interface 44.

The processor 42 is in BC module 46 configured to obtain a biomass content BC of biomass in the fermentation broth 16 in the fermentation tank 6 based on the first sensor data 12A from the first sensor 12 being an FTIR sensor and optionally the second sensor data 14A indicative of the amount of fermentation broth in the fermentation tank 6.

The processor 42 is in CIP module 48 configured to determine a carbon input parameter CIP, 4A based on the biomass content BC from BC module 46 and a feed rate FR.

The feed rate FR is determined in FR module 50 configured to determine the feed rate FR indicative of a carbon feed rate per biomass based on the biomass content BC and optionally one or more of a maximum feed rate FR_MAX, a maximum ammonia/carbon parameter ACP_MAX, and an ammonia/carbon parameter ACP. The processor 42 is optionally configured to determine a maximum feed rate in FR_MAX module 52 based on the biomass content BC. The maximum feed rate may be a default parameter stored in and retrieved from a memory of the feed control system. The processor 42 is optionally configured to determine a maximum ammonia/carbon parameter in ACP_MAX module 54 optionally based on a time since start of the fermentation. The maximum ammonia/carbon parameter may be a default parameter stored in and retrieved from a memory of the feed control system. The processor 42 is optionally configured to determine an ammonia/carbon parameter in ACP module 56, e.g. based on flow data 22A, 22B. The ammonia/carbon parameter may be given as the rate between the ammonia flow rate and the carbon flow rate.

The processor 42 is in CIP_MAX module 58 configured to determine a maximum carbon input parameter, e.g. given by equation (6) above as a function of time since start of the fermentation. The maximum carbon input parameter is output to CIP module 48 configured to determine and output carbon input parameter CIP, 4A based on the biomass content BC from BC module 46, the feed rate FR from FR module 50, and the maximum carbon input parameter CIP_MAX from CIP_MAX module 58, e.g. as given by equation (4) or optionally equation (5), where CIP_MIN is a default value or determined in a CIP_MIN module (not shown) of processor 42.

The processor 42 outputs the carbon input parameter CIP, 4A to the input source 10 to control a carbon input (carbon flow 18 from input source 10) to the fermentation broth 16 in the fermentation tank 6 according to the carbon input parameter 4A.

Figure 3:
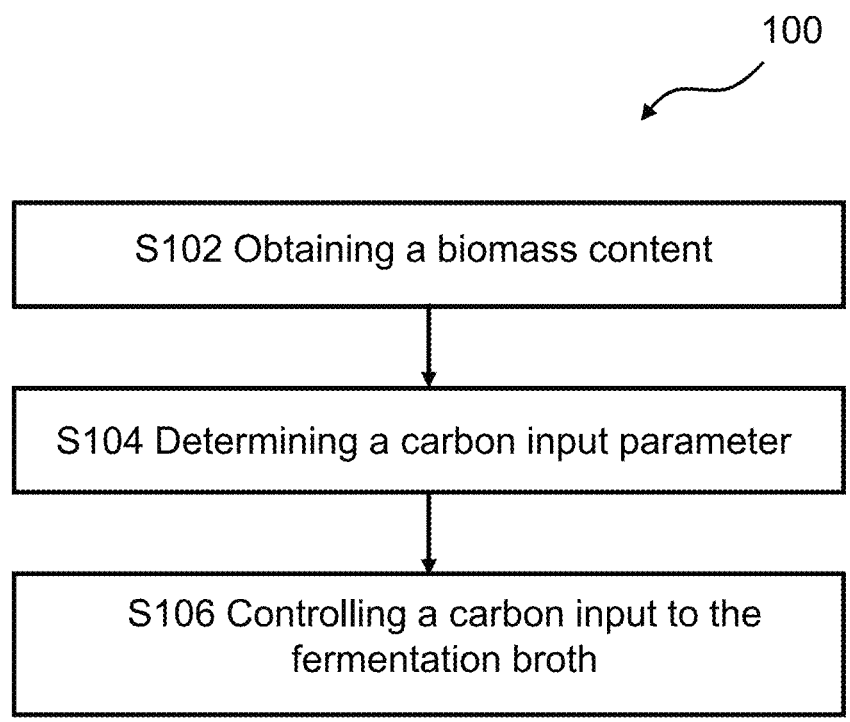
FIG. 3 is a flow chart of an exemplary method of producing human milk oligosaccharides.

FIG. 3 shows a flowchart of an exemplary method 100 performed by a feed control system for producing human milk oligosaccharides in a fermentation system. The method 100 comprises obtaining S102 a biomass content of a biomass in a fermentation broth, e.g. based on first sensor data 12A from first sensor 12, determining S104 a carbon input parameter based on the biomass content, and controlling S106 a carbon input to the fermentation broth according to the carbon input parameter, e.g. as described herein with reference to the feed control system.

Figure 4:
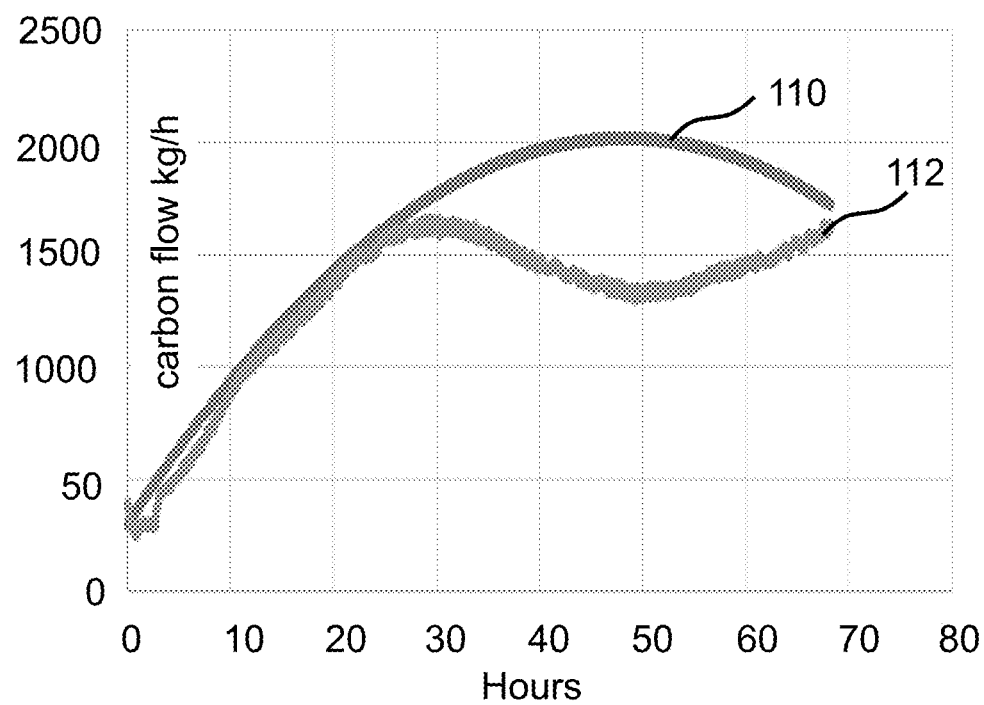
FIG. 4 illustrates the carbon feeding profiles of a predetermined standard feeding (110) and a feeding with an advanced feeding control system (112)

FIG. 4 shows a result of optimizing the carbon input parameter according to the present disclosure, where 110 shows a maximum carbon flow, and 112 shows carbon flow (carbon input parameter) for a fermentation batch optimized according to the present disclosure with a clear deviation from the flow profile 110 in the time period 30-70 hours.

Figure 5:
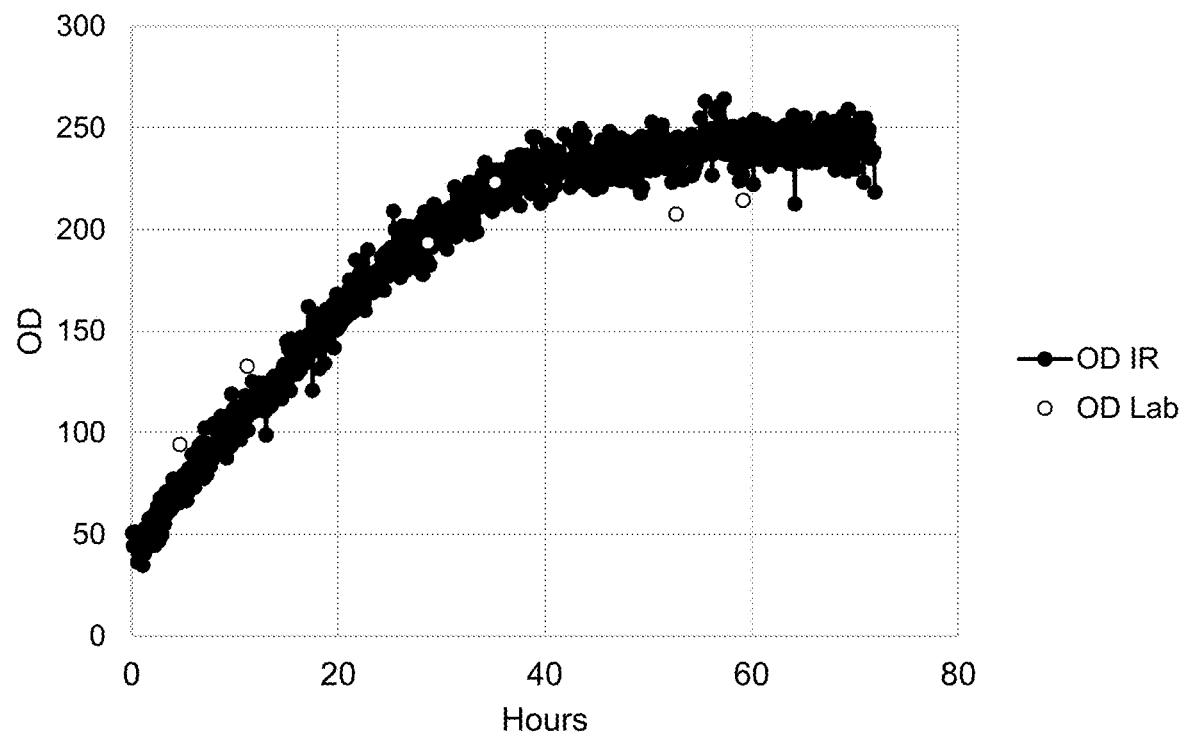
FIG. 5 illustrates the real-time online measurements of biomass using IRmadilloTM FTIR spectrometer (black closed dots) in relation to the off-line measurement of optical density (OD) at 600 (open white dots)

FIG. 5 illustrates the real-time online measurements of biomass using IRmadilloTM FTIR spectrometer (black closed dots) in relation to the off-line measurement of optical density (OD) at 600 (open white dots).

Figure 6:
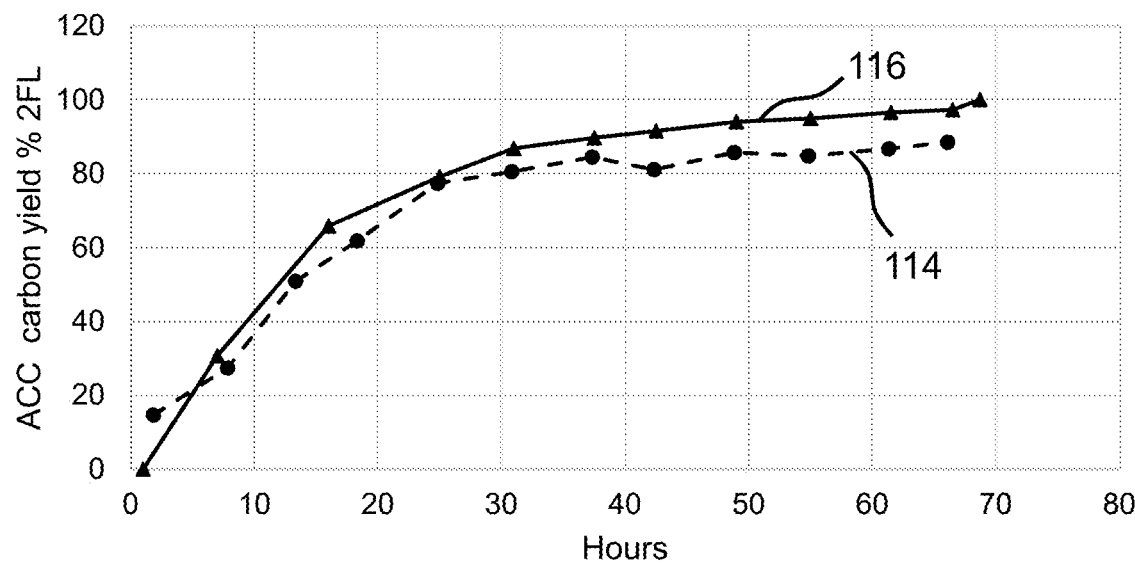
FIG. 6 illustrates the accumulated yield of product in % of utilized carbon source, where the yields are normalized with the maximum yield set to 100%.

FIG. 6 shows the accumulated yield of 2 fermentation batches, where yield profile 114 is yield using the fixed feeding profile 110 of FIG. 4 and yield profile 116 is yield using the carbon input profile 112 of FIG. 4, which is adapted and optimized according to the present disclosure. It is seen that a yield increase of about 10% is provided by the feed control system and method according to the present disclosure.

EXAMPLES

Materials and Methods

Unless otherwise noted, standard techniques, vectors, control sequence elements, and other expression system elements known in the field of molecular biology are used for nucleic acid manipulation, transformation, and expression. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); Bukhari et al. (eds.), *DNA Insertion Elements, Plasmids and Episomes* (1977) (Cold Spring Harbor Laboratory Press, NY); Miller, J. H. Experiments in molecular genetics (1972.) (Cold spring Harbor Laboratory Press, NY)

The embodiments described below are selected to illustrate the invention and are not limiting the invention in any way.

Strains

As background strain for the strain used in the example below the bacterial strain MDO, was used. MDO was constructed from *Escherichia coli* K-12 DH1. The *E. coli* K-12 DH1 genotype is: F−, λ-, gyrA96, recA1, relA1, endA1, thi-1, hsdR17, supE44. In addition to the *E. coli* K-12 DH1 genotype MDO has the following modifications: lacZ: deletion of 1.5 kbp, lacA: deletion of 0.5 kbp, nanKETA: deletion of 3.3 kbp, melA: deletion of 0.9 kbp, wcaJ: deletion of 0.5 kbp, mdoH: deletion of 0.5 kbp, and insertion of Plac promoter upstream of the gmd gene.

Methods of inserting gene(s) of interest into the genome of *E. coli* is well known to the person skilled in the art.

Insertion of genetic cassettes into the *E. coli* chromosome can be done using gene gorging (see for example Herring and Blattner 2004 J. Bacteriol. 186: 2673-81 and Warming et al 2005 Nucleic Acids Res. 33(4): e36) with specific selection marker genes and screening methods.

The 2'-FL strain used in Example 1 is based on the MDO strain and further contain the additional chromosomally integrated genes one extra colanic acid gene cluster (gmd-wcaG-wcaH-wcaI-manC-manB) under the control of a PglpF promoter at a locus that is different than the native locus, an α-1,2-fucosyltransferase from *Helicobacter pylori* (GenBank ID: WP_080473865.1, but with two additional amino acids (LG) at the C-terminus) under control of a PglpF promoter (SEQ ID NO: 12 in WO2019/123324) and a Major Facilitator Superfamily transporter protein from

*Rosenbergiella nectarea* (GenBank ID: WP_092672081.1) under control of a PglpF_SD7 promoter (SEQ ID NO: 19 of WO2019/123324).

Example 1-2'-FL Fermentation Process with and without Feed-Control

Standard 2'-FL Fermentation Process without Feed Control

A regular manufacturing scale fermentation with strain MP1 was carried out starting at a filling of approximately 75 tons (after inoculation from a seed fermenter) and ending above 300 tons of final broth. The fermentation basal medium was a fully defined minimal salt medium prepared with phosphoric acid (75%), KOH solution (45%), MgSO4, trace elements, citric acid, antifoam and thiamine. The medium pH was controlled at 6.8 by sparging of gaseous NH3 together with the inlet air. The ammonia also served as the only source of nitrogen. The trace elements included the elements Mn, Cu, Fe, Zn as sulfate salts, as well as Molybdate and Selenite. Lactose was added separately in a continuous fashion and was maintained at approximately 40 g/kg of broth throughout most of the fermentation, until the last day, when addition stopped and the ongoing conversion to 2'-FL caused the lactose to drop to below 10 g/kg. Aeration, stirring and overpressure were applied to control dissolved oxygen at 200% of air saturation, as measured by oxygen probes located at several places along the height of the fermenter. Fermentations were started by inoculation from a seed fermenter pre-culture, grown in a similar basal medium, which was supplemented with approximately 30 g of glucose as carbon and energy source/kg of medium. In the main fermenter, a sterile glucose feed solution (approximately 60% w/w) was fed continuously as the only source of carbon and energy at a pre-determined feeding profile (see FIG. 4, ref 110). The glucose feeding profile was originally designed to ensure carbon-limited conditions throughout the production phase in order to avoid overflow metabolism and acetic acid formation. Mineral salt levels were maintained by continuously feeding a separate co-feed solution to the fermenter, containing all the constituents of the basal medium. The fermentation temperature setpoint was dropped from 33 deg C. to 32 deg C. at approximately 30 h after inoculation. End-of-fermentation was at approximately 70 hours.

Throughout the fermentation, samples were taken in order to determine the concentration of 2'-FL, by-product DFL, lactose and other minor by-products using HPLC. Total broth samples were diluted three-fold in deionized water and boiled for 20 minutes, followed by centrifugation, whereafter the resulting supernatant was analysed by HPLC. The above measurements were used to accurately calculate the 2'-FL titer, the ratio of DFL/2'-FL and the accumulated yield of 2'-FL on the carbon source. The latter takes variations in feed rates, as expected during the use of the feed controller, into account and is therefore an important parameter for direct comparison between different batches.

Optimised 2'-FL Fermentation Process with Feed Control

As described in the present disclosure, an advanced feed control system was used to optimise the 2'-FL fermentation process using strain MP1. The fermentation was initiated as described for the standard fermentation process above. However, in this setup the feeding was adjusted according to various input parameters. The biomass input parameter (item S102, FIG. 3) was determined by applying real-time, in-situ measurement of biomass using an FTIR probe (IRmadillo™ by Keit Ltd., Didcot, Oxfordshire, UK). The FTIR instrument uses a probe which is autoclavable and positioned in the main fermenter. The FTIR instrument was trained for measuring biomass levels based on off-line OD measurements of a small number of calibration batches. The resulting real-time IRmadillo™ measurement of biomass of one exemplary 2'-FL manufacturing batch is depicted in FIG. 5.

As depicted in FIG. 3, the real-time biomass data (S102) was then used to calculate the corresponding carbon input parameter (S104), i.e., the biomass-specific sugar feed rate, also known as $q_S$. This parameter in turn was used to control the carbon input to the fermenter (S106). The resulting optimised feeding profile is depicted in FIG. 4 (ref 112).

FIG. 6 illustrates the accumulated yield of 2'-FL in % of utilized carbon source, where curve 116 is the yield with the controller optimized carbon feeding profile and curve 114 is the yield obtained with a pre-calculated standard feeding profile. The yields are normalized with the highest yield set to 100%. This clearly illustrates that the optimised carbon feeding profile leads to an approximately 10% improved accumulated yield of 2'-FL on the carbon source.

Example 2—Production of 2'-FL Using a Feed and Bleed Continuous Fermentation Setup and the Feed Control System The present example illustrates that the efficiency of a large scale fermentation process can be increased even further by extending the fermentation time by shifting from fed-batch fermentation to feed and bleed fermentation when the main fermentation vessel is reaching its maximum capacity.

The feed and bleed fermentation with strain MP1 was carried out at manufacturing scale starting with an initial broth mass of approximately 90 tons. The fermentation basal medium was identical to the medium used in Example 1. The fermentation was started by inoculation from a seed fermenter pre-culture, grown in a similar basal medium using a fed-batch approach to achieve a high cell concentration. After inoculation of the main fermenter, a sterile glucose feed solution was fed continuously as the only source of carbon and energy. The feeding rate was adjusted using the feed control system described in the optimised 2'-FL fermentation process of Example 1. Lactose was added separately in a continuous fashion and was maintained at a stable concentration of approximately 40 g/kg of broth until the last day when addition was stopped to allow the concentration to drop by the ongoing conversion to 2'-FL. Aeration, stirring and overpressure were applied to keep dissolved oxygen at a sufficient level to maintain fully respiratory metabolism. The mineral salt levels were maintained by continuously feeding a separate co-feed solution to the fermenter, containing all the constituents of the basal medium. For comparative purposes a fed-batch fermentation was made using the same protocol. The comparative fed-batch fermentation was stopped when the fermentation vessel reached approximately 310 tons after 56 hours.

Figure 7:
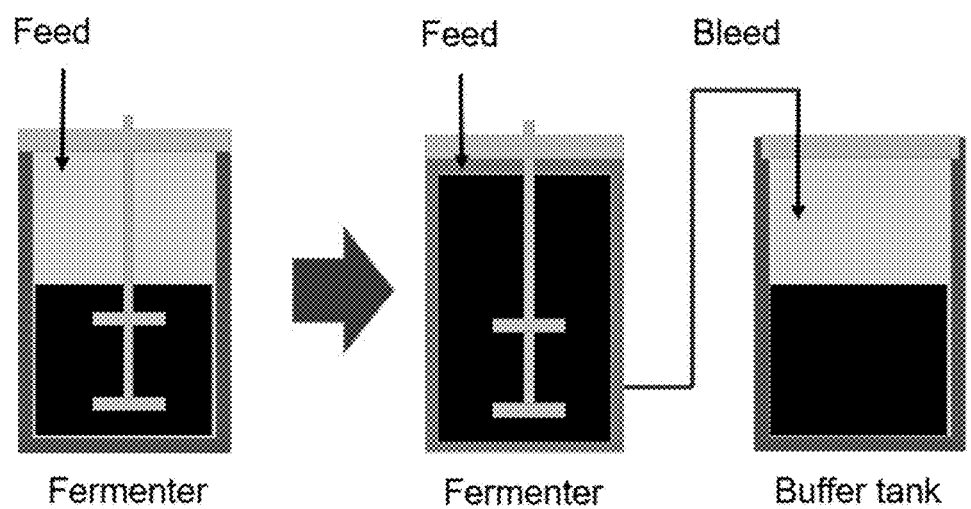
FIG. 7 illustrates a feed and bleed fermenter setup showing inlet and bleed streams of the fermenter. The horizontal arrow indicates the transition from fed-batch mode to feed and bleed mode.

For the feed and bleed fermentation, when the broth level in the fermentation vessel reached 310 tons a bleed stream was initiated, which dropped excess broth into a buffer tank to keep the vessel volume in the main fermenter between 310-240 tons (see FIG. 7). The fermentation was stopped when maximum productivity was reached after approximately 80 hours. At the end of fermentation, the final broth volume in the fermenter and buffer tank were 240 and 190 tons, respectively.

Throughout the fermentation, samples were taken in order to determine the concentration of 2'-FL, by-product DFL, lactose and other minor by-products using HPLC. Total broth samples were diluted three-fold in deionized water and boiled for 20 minutes, followed by centrifugation, whereafter the resulting supernatant was analysed by HPLC.

Figure 8:
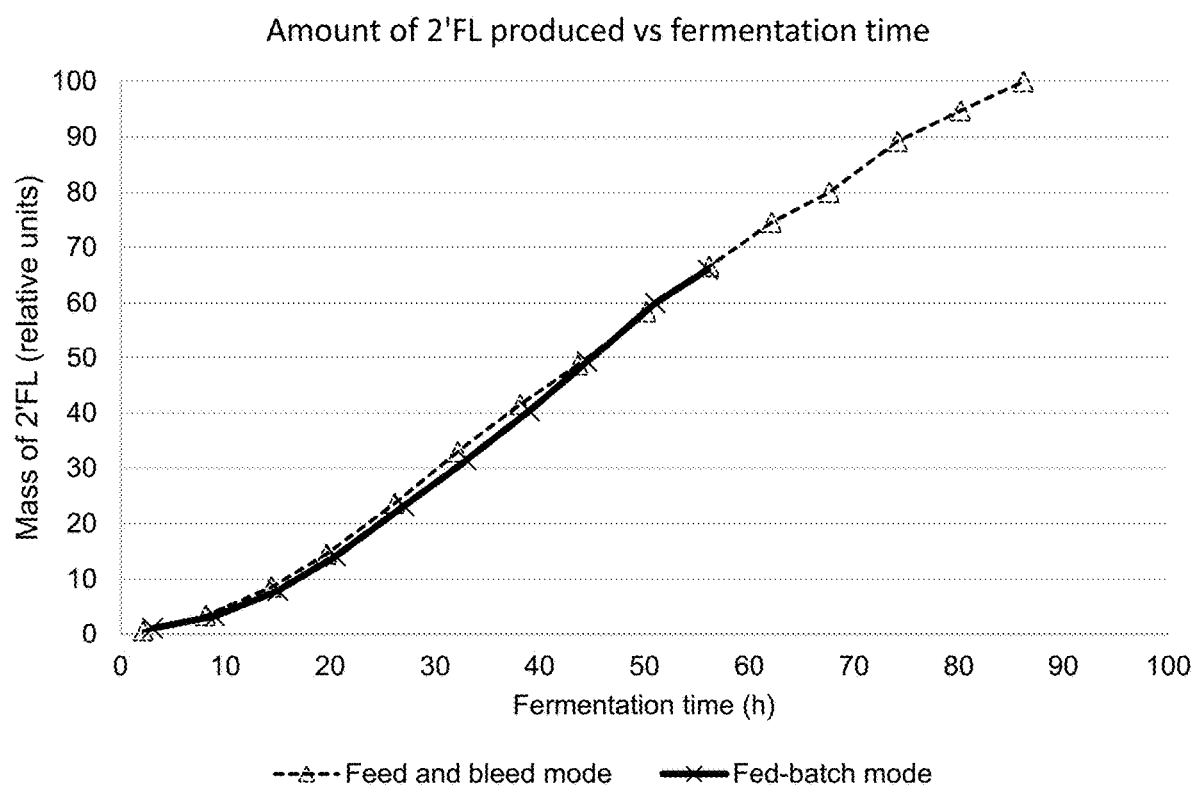
FIG. 8 illustrates the total amount of 2'-FL produced vs fermentation time of a fed-batch mode and a feed and bleed mode, where all numbers are normalized to the highest productivity.
Figure 9:
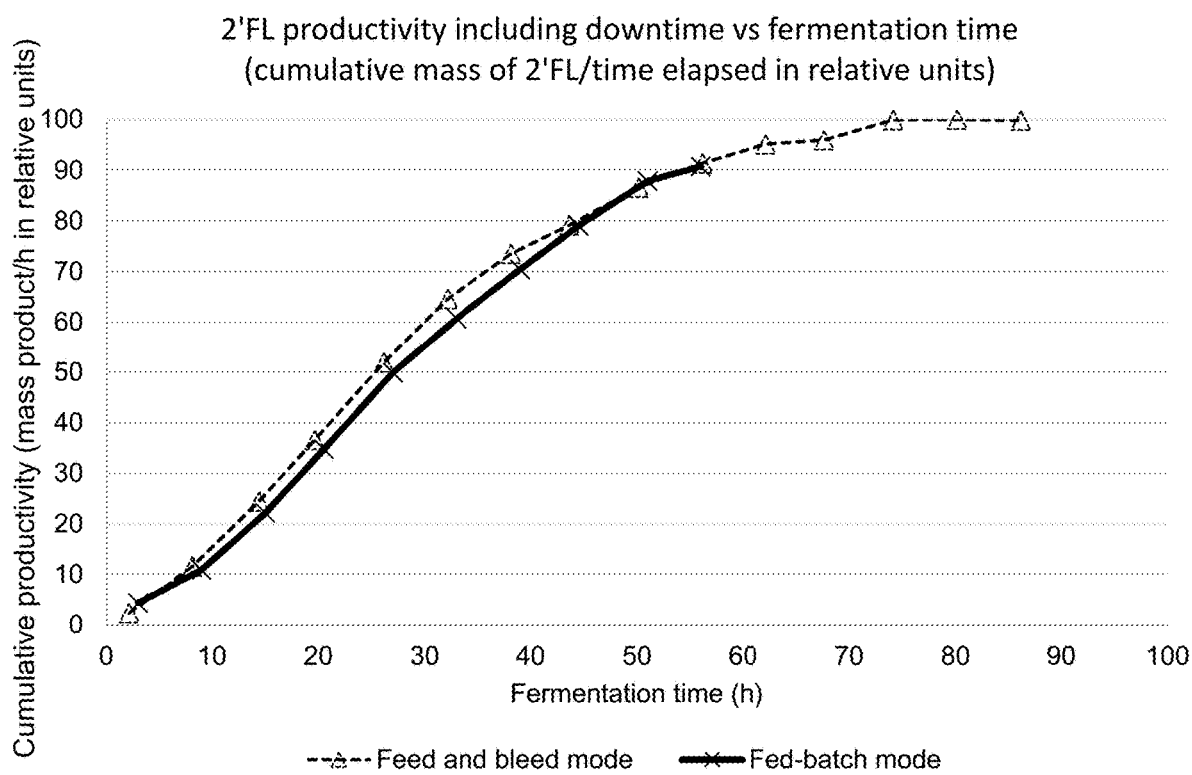
FIG. 9 illustrates the productivity of 2'-FL vs fermentation time including downtime of a fed-batch mode and a feed and bleed mode, where all numbers are normalized to the highest productivity.

Results:

The feed and bleed configuration allowed an extended HMO production at a high rate and a significantly increased batch size. The total amount of 2'-FL produced in one batch increased by 44% (FIG. 8.), whereas the overall productivity, including the downtime to restart the fermentation, increased by 10% (FIG. 9). The productivity including downtime is calculated as kg 2'-FL produced divided by the fermentation time plus 24 h downtime to restart the next fermentation.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Memory may be one or more of a buffer, a flash memory, a hard drive, a removable media, a volatile memory, a non-volatile memory, a random access memory (RAM), or other suitable device. In a typical arrangement, memory may include a non-volatile memory for long term data storage and a volatile memory that functions as system memory for the processor. Memory may exchange data with processor over a data bus. Memory may be considered a non-transitory computer readable medium.

Memory may be configured to store information (such as information indicative of the parameters and/or models of the feed control) in a part of the memory.

Furthermore, the labelling of a first element does not imply the presence of a second element and vice versa.

It may be appreciated that FIGS. 1-3 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 fermentation system
4 feed control system
4A carbon input parameter
6 fermentation tank
8 sensor system
10 carbon source supply system
12 first sensor, FTIR spectrometer
12A first sensor data, spectrometer data indicative of biomass content
12B optical density probe
14 second sensor
14A second sensor data
16 fermentation broth
18 carbon flow
20 carbon input
22 first flow sensor
22A first flow data
24A, 24B, 24C, 24D data connection
26 ammonia source, pH regulator
26A ammonia input parameter
28 ammonia flow
30 ammonia input
32 second flow sensor
32A second flow data
34 tank output
40 feed controller
42 processor of feed controller
44 interface of feed controller
46 BC module or circuitry for obtaining/determining/calculating biomass content
48 CIP module or circuitry for determining/calculating carbon input parameter
50 FR module or circuitry for determining/calculating feed rate 52 FR_MAX module or circuitry for determining/calculating maximum feed rate
54 ACP_MAX module or circuitry for determining/calculating maximum ammonia/carbon parameter
56 ACP module or circuitry for obtaining/determining/calculating ammonia/carbon parameter
58 CIP_MAX module or circuitry for determining/calculating maximum carbon input parameter
100 a method performed by a feed control system for producing human milk oligosaccharides in a fermentation system
110 carbon flow profile
112 optimized carbon flow profile
114 yield profile of a carbon flow
116 yield profile of an optimized carbon flow profile
S102 obtaining a biomass content of a biomass in a fermentation broth
S104 determining a carbon input parameter based on the biomass content
S106 controlling a carbon input to the fermentation broth according to the carbon input parameter

The invention claimed is:

1. A feed control system for a fermentation system, the feed control system comprising a feed controller comprising a processor and an interface, wherein the processor is configured to:
obtain a biomass content in a fermentation broth based on first sensor data from a first sensor device;
determine a carbon input parameter based on the biomass content comprising determining a feed rate indicative of a carbon feed rate per biomass and determining a carbon input parameter based on the feed rate and the biomass content; and
control a carbon input to the fermentation broth according to the carbon input parameter.

2. The feed control system according to claim 1, wherein to determine the carbon input parameter based on the feed rate and the biomass content comprises to determine a preliminary carbon input parameter based on the feed rate and the biomass content, and wherein the carbon input parameter is based on the preliminary carbon input parameter.

3. The feed control system according to claim 2, wherein to determine the carbon input parameter comprises to set the preliminary carbon input parameter as the carbon input parameter in accordance with the preliminary carbon input parameter satisfying a carbon input criterion and to set a default carbon input parameter as the carbon input parameter in accordance with the preliminary carbon input parameter not satisfying the carbon input criterion.

4. The feed control system according to claim 1, wherein to determine the feed rate indicative of a carbon feed rate per biomass comprises to apply a yield model for provision of a preliminary feed rate, the yield model taking the biomass content as input, and wherein the feed rate is based on the preliminary feed rate.

5. The feed control system according to claim 4, wherein to determine a feed rate indicative of a carbon feed rate per biomass comprises to determine a maximum feed rate and wherein the feed rate is based on the maximum feed rate.

6. The feed control system according to claim 5, wherein to determine a feed rate comprises to set the preliminary feed rate as the feed rate in accordance with the preliminary feed rate satisfying a feed rate criterion and to set a default feed rate as the feed rate in accordance with the preliminary feed rate not satisfying the feed rate criterion.

7. The feed control system according to claim 1, wherein the processor is configured to obtain an ammonia/carbon parameter, and wherein the feed rate is based on the ammonia/carbon parameter.

8. The feed control system according to claim 7, wherein the processor is configured to determine a maximum ammonia/carbon parameter, and wherein the feed rate is based on the ammonia/carbon parameter and the maximum ammonia/carbon parameter.

9. The feed control system according to claim 8, wherein the maximum ammonia/carbon parameter is based on a time parameter indicative of a start of fermentation.

10. The feed control system according to claim 1, wherein the feed control system comprises a Fourier Transform Infrared (FTIR) spectrometer connected to the feed controller for provision of spectrometer data indicative of the biomass content.

11. The feed control system according to claim 1, wherein the processor is configured to obtain the biomass content in the fermentation broth at least once every 4 hours least two times per hour.

12. The feed control system according to claim 1, wherein the fermentation system is for the production of one or more human milk oligosaccharides.

13. The feed control system according to claim 12, wherein the fermentation system is in a continuous or semi-continuous mode.

14. A method of producing a heterologous product by a feed control system in a fermentation system, the method comprising:
obtaining a biomass content in a fermentation broth comprising a host cell capable of producing the heterologous product, wherein the biomass content is based on first sensor data from a first sensor device;
determining a carbon input parameter based on the biomass content, wherein determining a carbon input parameter comprises (a) determining a feed rate indicative of a carbon feed rate per biomass and (b) determining a carbon input parameter based on the feed rate and the biomass content; and
controlling a carbon input to the fermentation broth according to the carbon input parameter.

15. The method according to claim 14, wherein the carbon input parameter based on the biomass content is determined using a feed control system comprising a feed controller comprising a processor and an interface, wherein the processor is configured to:
obtain a biomass content in a fermentation broth based on first sensor data from a first sensor device;
determine a carbon input parameter based on the biomass content comprising determining a feed rate indicative of a carbon feed rate per biomass and determining a carbon input parameter based on the feed rate and the biomass content; and
control a carbon input to the fermentation broth according to the carbon input parameter.

16. The method according to claim 14, wherein the carbon input to the fermentation broth according to the carbon input parameter is controlled using a feed control system comprising a feed controller comprising a processor and an interface, wherein the processor is configured to:
obtain a biomass content in a fermentation broth based on first sensor data from a first sensor device;
determine a carbon input parameter based on the biomass content comprising determining a feed rate indicative of a carbon feed rate per biomass and determining a carbon input parameter based on the feed rate and the biomass content; and control a carbon input to the fermentation broth according to the carbon input parameter.

17. The method according to claim 14, wherein the heterologous product is one or more human milk oligosaccharides.

18. The method according to claim 14, wherein the host cell is *E. coli*.

19. The method according to claim 14, wherein the method comprises,
   a) providing a first primary bioreactor comprising a liquid nutrient media,
   b) adding to said first primary bioreactor a carbon source,
   c) inoculating the first primary bioreactor with one or more heterologous product producing microorganism(s),
   d) fermenting the added carbon source to produce a fermentation broth comprising at least one or more heterologous product producing microorganism(s) and one or more heterologous product(s),
   e) passing at least a portion of the fermentation broth from the first primary bioreactor, via a central bleed line into at least one other bioreactor and/or storage tank,
   f) adding at least a portion of additional liquid nutrient media and/or carbon source to the first primary bioreactor,
   g) operating the first primary bioreactor at conditions to promote growth of microorganisms and to promote heterologous product production from said microorganism and optionally,
   h) harvesting and/or purifying of the one or more heterologous product(s) from the fermentation broth.

20. The method according to claim 19, wherein a substrate is fed together with the carbon source in step b), either as a separate feed or together with the carbon source.

21. The method according to claim 19, wherein step e) is initiated when the volume of the first primary bioreactor is between 80 and 100%.

* * * * *